United States Patent
Raz

(10) Patent No.: US 7,734,840 B2
(45) Date of Patent: Jun. 8, 2010

(54) METHODS AND SYSTEMS FOR MANAGING OUTPUTS TO PERIPHERAL DEVICES

(75) Inventor: Israel Raz, Highland Park, IL (US)

(73) Assignee: GE Medical Systems Global Technology Co., LLC, Waukesha, WI (US)

( * ) Notice: Subject to any disclaimer, the term of this patent is extended or adjusted under 35 U.S.C. 154(b) by 370 days.

(21) Appl. No.: 10/722,914

(22) Filed: Nov. 26, 2003

(65) Prior Publication Data

US 2005/0114568 A1    May 26, 2005

(51) Int. Cl.
G06F 3/00 (2006.01)
G06F 13/12 (2006.01)

(52) U.S. Cl. .............................. 710/15; 710/17; 710/52

(58) Field of Classification Search ..................... 710/8, 710/15–17, 19, 31, 33, 52
See application file for complete search history.

(56) References Cited

U.S. PATENT DOCUMENTS

| | | | | |
|---|---|---|---|---|
| 5,898,824 A * | 4/1999 | Kato et al. | ................. | 358/1.16 |
| 6,023,343 A * | 2/2000 | Hoang et al. | ................ | 358/1.16 |
| 6,238,344 B1 | 5/2001 | Gamelsky et al. | | |
| 6,241,673 B1 | 6/2001 | Williams | | |
| 6,358,204 B1 | 3/2002 | Finger et al. | | |
| 6,401,150 B1 * | 6/2002 | Reilly | ......................... | 710/104 |
| 6,614,559 B2 * | 9/2003 | Olin | ............................ | 358/403 |
| 7,019,863 B2 * | 3/2006 | Mathieson | ................. | 358/1.16 |
| 7,180,619 B2 * | 2/2007 | Ferlitsch | .................... | 358/1.15 |
| 2001/0040691 A1 * | 11/2001 | Sakamoto | .................. | 358/1.14 |
| 2002/0063880 A1 * | 5/2002 | Raney | ........................ | 358/1.14 |
| 2003/0051050 A1 * | 3/2003 | Adelaide et al. | ............ | 709/238 |
| 2003/0053109 A1 * | 3/2003 | Lester et al. | ................ | 358/1.14 |
| 2004/0084971 A1 * | 5/2004 | Shukla et al. | ................ | 307/126 |
| 2004/0139265 A1 * | 7/2004 | Hocker et al. | ................ | 710/305 |
| 2005/0114568 A1 * | 5/2005 | Raz | ............................. | 710/52 |
| 2008/0180701 A1 * | 7/2008 | Nakagiri et al. | .............. | 358/1.9 |

OTHER PUBLICATIONS

Accessible—Definition from the Merriam-Webster Online Dictionary.pdf—http://www.merriam-webster.com/cgi-bin/dictionary?book=Dictionary&va=accessible.*
French Search Report, Paris, Sep. 2, 2005, 2 pages.

* cited by examiner

*Primary Examiner*—Niketa I Patel
*Assistant Examiner*—David E Martinez
(74) *Attorney, Agent, or Firm*—Dean Small; Small Patent Law Group

(57) ABSTRACT

A method for managing outputs to peripheral devices in medical systems devices is described. The method includes providing an instruction to provide an output, creating a data object based on the instruction, and storing the data object in a first memory if a peripheral device that provides the output is not available to accept the data object, where the first memory stores the data object for a longer term than a second memory.

21 Claims, 4 Drawing Sheets

METHODS AND SYSTEMS FOR MANAGING OUTPUTS TO PERIPHERAL DEVICES

BACKGROUND OF THE INVENTION

This invention relates generally to imaging systems and more particularly to methods and systems for managing outputs to peripheral devices used with the imaging systems.

In clinical ultrasound system applications, information relating to test results is often output to peripheral devices for a specific purpose. For example, the information may be output for communicating results, use in consulting with an expert, printing reports, maintaining backups, and archiving. There are circumstances when the peripheral devices may not be available during an examination, for example, when using a portable ultrasound imaging system. Portable ultrasound imaging systems are designed to address needs for mobile testing within, for example, a hospital, in satellite clinics, and in critical care environments.

However, to minimize system size and weight of these portable devices, built-in removable media, which is used to transfer data from the ultrasound imaging system to the peripheral devices, usually is not included. Moreover, portability may be reduced if an operator takes several peripheral devices, such as a printer, a VCR, or a CD/MO/DVD writer, with the portable ultrasound imaging system in order to output information. On the other hand, if the peripheral devices are not immediately available (e.g., portable devices without peripherals), information cannot be output from the device until the operator connects the peripheral devices to the ultrasound imaging system and provides instructions for outputting the information. Thus, productivity and efficiency may be reduced.

BRIEF DESCRIPTION OF THE INVENTION

In one aspect, a method for managing outputs to peripheral devices in medical systems devices is provided. The method includes providing an instruction to provide an output, creating a data object based on the instruction, and storing the data object in a first memory if a peripheral device that provides the output is not available to accept the data object, where the first memory stores the data object for a longer term than a second memory.

In another aspect, an imaging system is provided. The imaging system includes a source for transmitting signals, and a processor operationally coupled to the source. The processor is configured to receive an instruction to provide an output, create a data object based on the instruction, and instruct to store the data object in a first memory if a peripheral device that provides the output is not available to accept the data object, where the first memory stores the data object for a longer term than a second memory.

In yet another aspect, a computer-readable medium encoded with a program is provided. The program is configured to receive an instruction to provide an output, create a data object based on the instruction, and instruct to store the data object in a first memory if a peripheral device that provides the output is not available to accept the data object, where the first memory stores the data object for a longer term than a second memory.

DETAILED DESCRIPTION OF THE INVENTION

Figure 1:
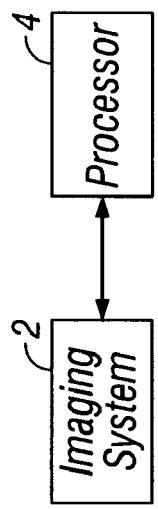
FIG. 1 is a simplified block diagram of an exemplary embodiment of an imaging system in which systems and methods for managing outputs to peripheral devices of various embodiments of the invention may be implemented.

FIG. 1 shows an exemplary embodiment of an imaging system 2 in which systems and methods for managing outputs to peripheral devices are implemented. Examples of imaging system 2 include an ultrasound imaging system, electron-beam tomography (EBT) imaging system, magnetic resonance imaging (MRI) system, single photon emission computed tomography (SPECT) imaging system, computed tomography (CT) imaging system, and positron emission tomography (PET) imaging system, among others. A processor 4 is operationally coupled to the imaging system 2, for example, via a wireless or a wired connection. In an alternative embodiment, processor 4 is located within imaging system 2. The processor 4 receives data from imaging system 2 and executes a method for managing outputs to peripheral devices as described herein.

Figure 2:
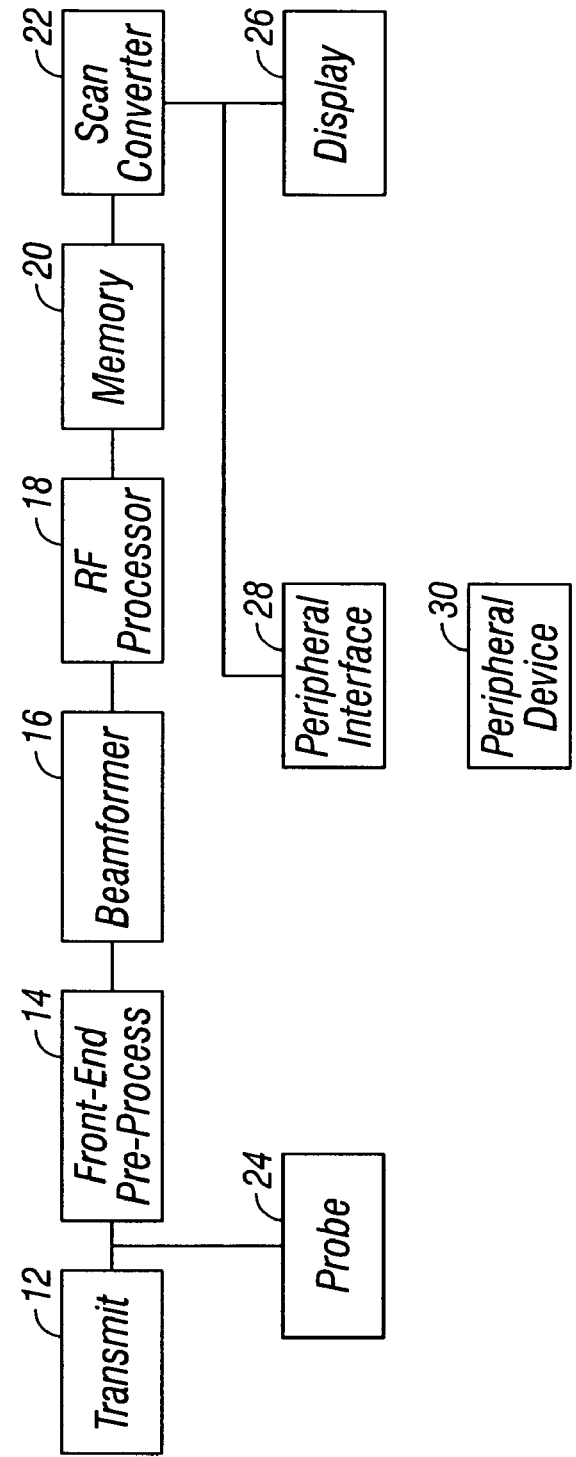
FIG. 2 is a block diagram of an exemplary embodiment of an ultrasound imaging system in which systems and methods for managing outputs to peripheral devices may be implemented.

FIG. 2 is a block diagram of an exemplary embodiment of an ultrasound imaging system 10 in which systems and methods for managing outputs to peripheral devices may be implemented. An example of the ultrasound imaging system 10 is an ultrasound imaging system that does not include built-in removable media. Examples of built-in removable media include a floppy disk, an analog video cassette, an analog audio cassette, a digital versatile device, an optical disk, a DVD, a removable hard disk, and a flash memory card.

The ultrasound imaging system 10 can be a portable or a non-portable imaging system. The ultrasound imaging system 10 includes a transmitter 12, a front-end pre-processor 14, a beamformer 16, a radio frequency (RF) processor 18, a memory 20, a scan converter 22, a transducer, referred to as an ultrasound probe 24, a display device 26, and a peripheral interface 28. Examples of the display device 26 include a cathode ray tube (CRT) and a liquid crystal display (LCD) monitor. Examples of peripheral interface 28 include a network card, a bluetooth interface, a universal serial bus (USB), a parallel port, and a serial port. Examples of peripheral device 30 include a printer, an analog video cassette recorder (VCR), and digital storage media, such as, a CD-RW, a DVD rewriteable (DVD-RW), a floppy disk drive, an optical disk drive, a removable hard disk drive, a network, and a flash memory card drive, among others.

Transmitter 12 transmits pulsed ultrasonic signals via the ultrasound probe 24. Ultrasound probe 24 includes a transducer or a plurality of transducers that emit the pulsed ultrasonic signals into a region of interest, such as, for example, a patient's chest. Structures, such as a heart, blood cells, or muscular tissue, in region of interest back-scatter the ultrasonic signals to generate echoes which return to the ultrasound probe 24.

The front-end pre-processor 14 receives the echoes via the ultrasound probe 24 and generates electrical signals having information relating to structures in the region of interest. The front-end pre-processor 14 processes, such as, amplifies, the signals to provide an output. The beamformer 16 receives the output from the front-end pre-processor 14 and processes the output by digitizing the output, and performing steering or focusing operations to generate receive beams. The receive beams are processed by RF processor 18 or a complex demodulator (not shown) that demodulates the receive beams and forms in-phase and quadrature (I/Q) data pairs. Moreover, filtering and compression operations can also be performed by the RF processor 18. An output of the RF processor 18 is routed to memory 20 for storage. The scan converter 22 receives the output from RF processor 18 and converts the output into an image for display. The display device 26 receives the image and displays the image. The peripheral device 30 that can be coupled to ultrasound imaging system 10 via the peripheral interface 28 is used to perform various operations on the image. For instance, the peripheral device 30 is used to print the image. As another instance, the peripheral device 30 may be used to store a copy of the image on a CD.

Figure 3:
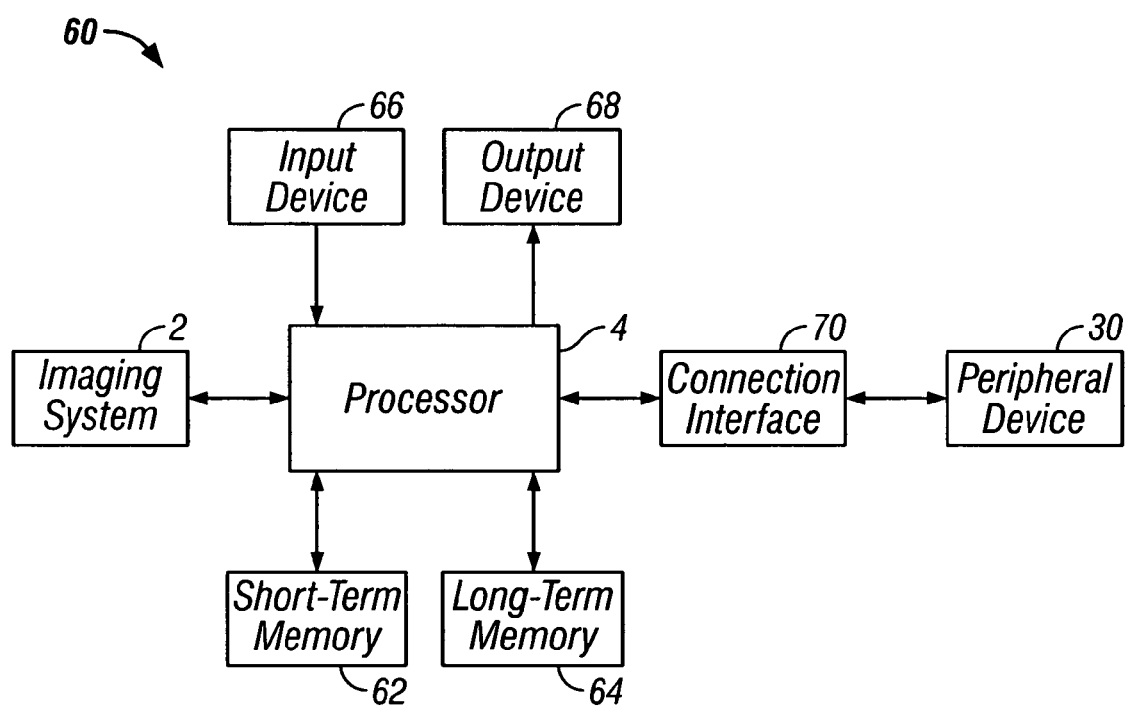
FIG. 3 is a block diagram of an exemplary embodiment of a system for managing outputs to peripheral devices.

FIG. 3 is an exemplary embodiment of a system 60 for managing outputs to peripheral devices. System 60 includes imaging system 2, processor 4, a short-term memory 62, a long-term memory 64, an input device 66, an output device 68, a connection interface 70, and one or more peripheral device 30. Examples of input device 66 include a keyboard, a mouse, and a trackball. Examples of output device 68 include display 36. Examples of short-term memory 62 include a buffer and a volatile memory, such as a random access memory (RAM). Examples of long-term memory 64 include a non-volatile memory such as a read-only memory (ROM) and a RAM powered with a battery. Other examples of non-volatile memory include a hard disk, a digital versatile disc (DVD), a compact disc rewriteable (CD-RW), and a memory stick. Examples of ROM include a programmable ROM (PROM), an erasable programmable ROM, and an electrically erasable PROM (EEPROM). Long-term memory 64 can store data objects and access the data objects when processor 4 or imaging system 2 when needed or desired. An example of a data object is digitally formatted data object, such as a file. Processor 4 is not limited to integrated circuits referred to in the art as computers, but broadly refer to computers, microcontrollers, microcomputers, programmable logic controllers, application specific integrated circuits, and other programmable circuits, among others, and these terms are used interchangeably herein. Examples of connection interface 70 include a network card, a bluetooth interface, a universal serial bus (USB), a parallel port, and a serial port.

Imaging system 2 scans a subject, such as a patient, to obtain data, such as, for instance, image data. Processor 4 receives the data from imaging system 2 and outputs the data, such as, video signals or information regarding a patient scanned using imaging system 2, to output device 68. Output device 68 displays the processed data in various forms, such as, images or cine loops.

Figure 4:
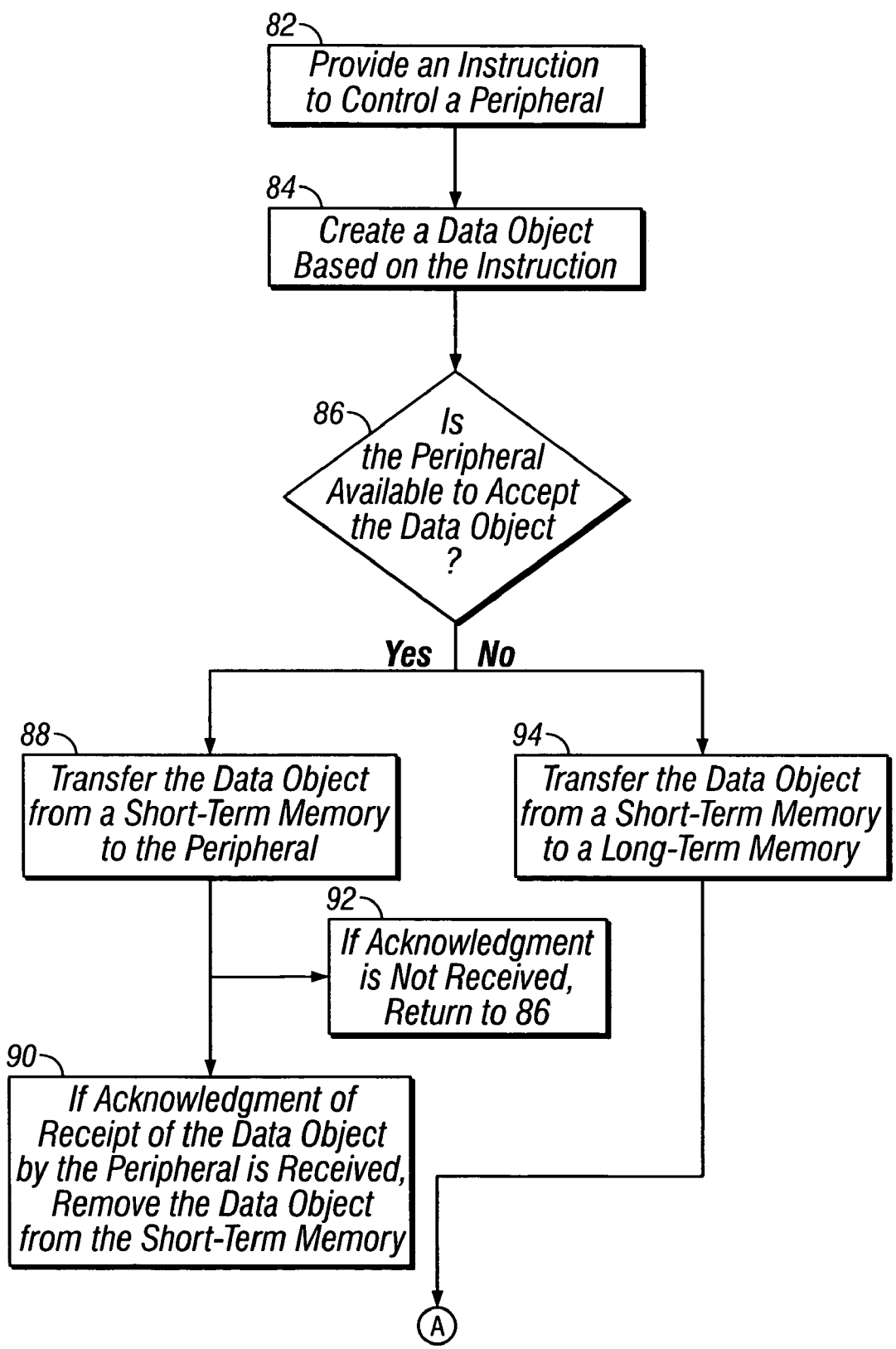
FIGS. 4 and 5 are a flowchart of an exemplary embodiment of a method for managing outputs to peripheral devices.
Figure 5:
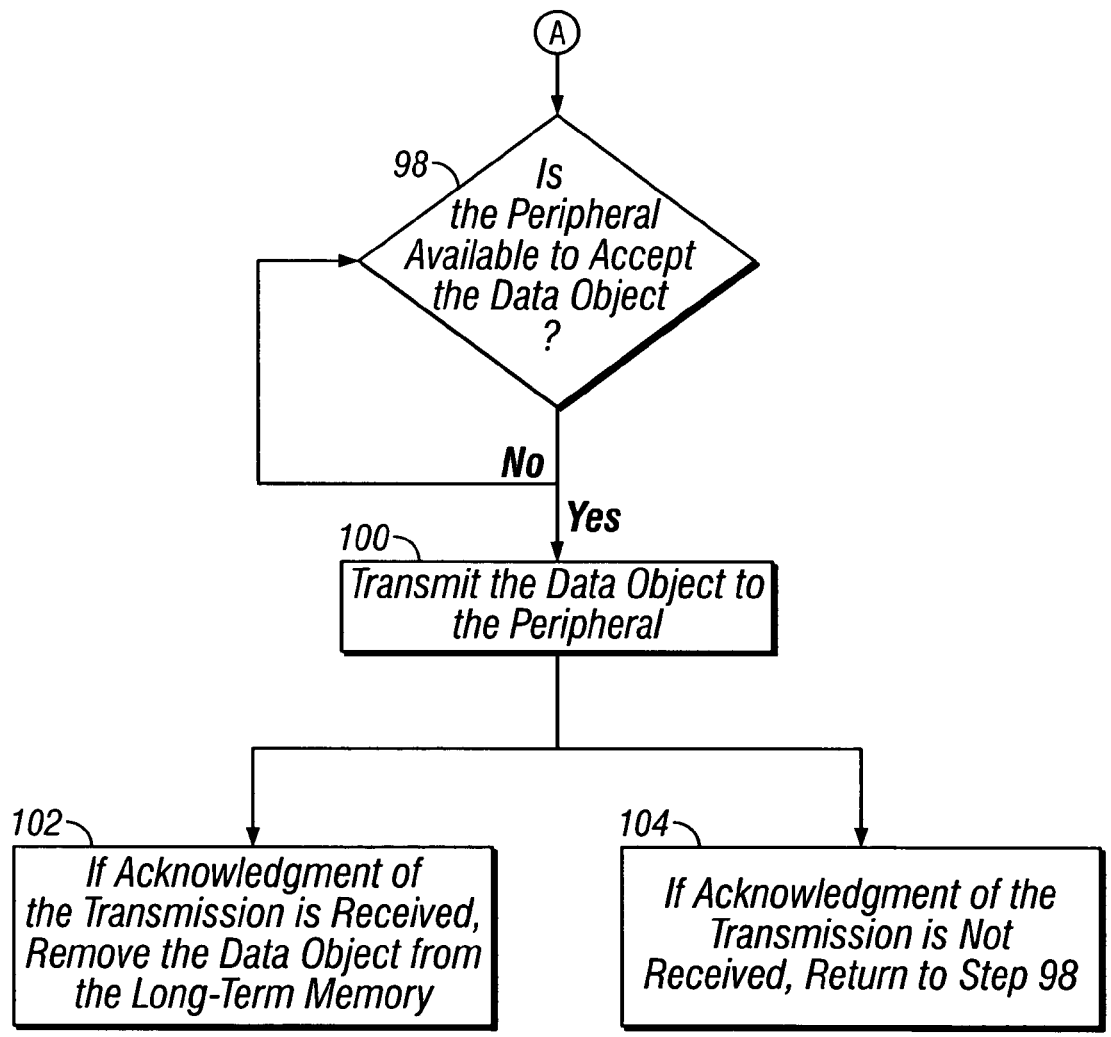

FIGS. 4 and 5 is a flowchart of an embodiment of a method for managing outputs to peripheral devices, for example, executed by using the system 60 shown in FIG. 3. At 82, an operator of imaging system 2 (shown in FIG. 3) provides an instruction to peripheral device 30 (shown in FIG. 3) that provides an output representative of the processed data. As an example, the operator selects "print" on an input device 66 (shown in FIG. 3). Such as, for example, a keyboard. In this example, by selecting "print", the operator instructs the peripheral device 30, such as a printer, to print the processed data. In this example, peripheral device 30 provides a printed copy of the processed data as an output. As another example, the operator selects a "record" button on output device 68. In the example, by selecting "record", the operator instructs peripheral device 30, such as, for example, a VCR, to record the processed data. In this example, peripheral device 30 provides cine loops as an output. As yet another example, the operator selects a "send e-mail" button on output device 68 after attaching a copy of the processed data to the e-mail. In the example, by selecting "send e-mail", the operator instructs peripheral device 30, such as a node within a network, to e-mail the copy of the processed data. In this example, peripheral device 30 enables processor 4 to e-mail the copy of the processed data to another processor (not shown). As still another example, the operator selects a "save" or a "save as" button on output device 68. In the example, by selecting the "save" or the "save as" button, the operator instructs peripheral device 30, such as, for example, a CD-RW, a DVD-RW, a floppy disk drive, an optical disk drive, a removable hard disk drive, or a flash memory card drive, to create and store a copy of the processed data. In the example, peripheral device 30 creates and stores the copy of the processed data. One of the most important examples (may be should be listed first) is the instruction to print a report on the patient's examination. This is a must in order to get reimbursement.

At 84, processor 4 creates a data object based on the instruction. For example, if the instruction is to print, processor 4 creates a print data object that can instruct peripheral device 30 to print. If the instruction is to record on a VCR, processor 4 creates a record data object that can instruct peripheral device 30, such as a VCR, to record. If the instruction is to e-mail a copy of the processed data, processor 4 creates an e-mail data object that can instruct peripheral device 30 to e-mail the copy of the processed data. If the instruction is to create and store a copy of the processed data, processor 4 creates a copy data object that can instruct peripheral device 30 to create and store a copy of the processed data.

Processor 4 transmits the data object created based on the instruction to short-term memory 62 (shown in FIG. 3) that sends the data object to connection interface 70. Connection interface 70 attempts to send the data object to peripheral device 30.

At 86, processor 4 (shown in FIG. 3) determines whether peripheral device 30 is available to accept the data object. As an example, processor 4 determines whether peripheral device 30 is available by determining whether peripheral device 30 is operationally coupled to processor 4 via connection interface 70. As another example, processor 4 determines whether peripheral device 30 is available by determining whether the processor has a wired connection with a printer via a parallel port. As yet another example, processor 4 determines whether peripheral device 30 is available by determining whether the processor 4 is connected via a wire or a wireless connection to a network that is connected via a wired or a wireless connection to the peripheral device. As still another example, processor 4 determines whether peripheral device 30 is available by determining whether the processor has a wired connection to a VCR. As another example, processor 4 determines whether peripheral device 30 is available by determining whether the processor has a wired connection to a CD-RW, a DVD-RW, a floppy disk drive, an optical disk drive, a removable hard disk drive, or a flash memory card drive. It is noted that one or multiple peripheral devices can be operationally coupled to processor 4 via connection interface 70 at the same time. Alternatively or in addition, processor 4 determines whether peripheral device 30 is available by determining whether peripheral device 30 is in an active state (e.g., turned on or energized). Alternatively or in addition, processor 4 determines whether peripheral device 30 is available by determining whether the peripheral device is properly functioning or not malfunctioning. Alternatively or in addition, processor 4 determines whether peripheral device 30 is available by determining whether the peripheral device 30 is busy performing other operations.

If processor 4 determines that peripheral device 30 is available to accept the data object, the processor, at 88, transfers or moves the data object from short-term memory 62 via connection interface 70 to peripheral device 30. When peripheral device 30 receives the data object, the peripheral device verifies or acknowledges receipt of the data object to processor 4. On receiving the acknowledgment, in an exemplary embodiment, processor 4, at 90, removes the data object from short-term memory 62. As an example, processor 4 removes a print job from a job queue on receiving an acknowledgment that peripheral device 30 has received a print data object. In an alternative exemplary embodiment, on receiving the acknowledgment, processor 4 removes the data object from short-term memory 62. If processor 4 does not receive the acknowledgment from peripheral device 30, at 92, a determination is again made at 86 as to whether the peripheral device 30 is available to accept the data object.

If the processor 4 determines that peripheral device 30 is not available to accept the data object, the processor, at 94, transfers the data object from short-term memory 62 to long-term memory 64. In an alternative embodiment, if processor 4 determines that peripheral device 30 is not available to accept the data object, the processor copies the data object from short-term memory 62 to long-term memory 64.

If the peripheral 30 is not available, in an exemplary embodiment, the operator accesses the data object stored in long-term memory 64, determines whether the peripheral device 30 is now available to accept the data object, and, if so, instructs processor 4 to transmit the data object via connection interface 70 to peripheral device 30. In an exemplary embodiment, processor 4 automatically determines, at 98, whether the peripheral device 30 is available to accept the data object stored in long-term memory 64, and if so, accesses the data object from the long-term memory, and transmits, at 100, the data object to peripheral device 30 via connection interface 70.

When peripheral device 30 receives the data object, the peripheral device 30 acknowledges receipt of the data object to processor 4. On receiving the acknowledgment, in an exemplary embodiment, processor 4, at 102, removes the data object from long-term memory 64. As an example, processor 4 removes a print job from a job queue on receiving an acknowledgment that peripheral device 30 has received a print data object. In an alternative exemplary embodiment, on receiving the acknowledgment, processor 4 removes the data object from short-term memory 62 and long-term memory 64 if the data object is copied from short-term memory 62 to long-term memory 64 instead of being transferred at 94. If processor 4 does not receive the acknowledgment from peripheral device 30, at 104, a determination is again made at 98 as to whether the peripheral 30 is available to accept the data object.

Upon receiving the data object, the peripheral device 30 executes the instruction based on which the data object is created. The peripheral device 30 also may acknowledge execution of the instruction to processor 4.

Technical effects of the systems and methods for managing outputs include eliminating various operations that the operator performs on returning to a facility, such as a hospital, after a traveling period during which data is collected from imaging system 2. The operations include, for example, accessing an application program, searching for a correct patient record, preparing an output based on the patient record, and sending the output to peripheral device 30. The operations are reduced and/or eliminated because the data object is saved in long-term memory 64 and on determining that peripheral device 30 is available, the data object is sent to the peripheral device to execute the instruction based on which the data object is created. Other technical effects of the herein described systems and methods include increasing productivity with no affects in portability of imaging system 2, eliminating workflow downtime if peripheral device 30 is malfunctioning, using the same peripheral devices during and after travel, saving significant time delays between examination of the subject and output by the peripheral device, and increasing workflow efficiency.

Although the herein described methods are described in a medical setting, the various embodiments described herein may be implemented in non-medical imaging systems such as those systems typically employed in an industrial setting or a transportation setting, such as, for example, but not limited to, a baggage scanning system for an airport, other transportation centers, government buildings, office buildings, and the like. The various embodiments described herein may also be implemented in micro PET and CT systems that are sized to study lab animals as opposed to humans. Further, additional or different component parts may be provided as desired or needed. Modifications, to the herein described component also may be provided. Moreover, the herein described systems and methods can be used with operating systems, such as Windows™ 2000 Windows™ XP™, Linux™, VMS™, OS/400™, AIX™, and z/OS™ located within processor 4.

While the invention has been described in terms of various specific embodiments, those skilled in the art will recognize that the invention can be practiced with modification within the spirit and scope of the claims.

What is claimed is:

1. A method for managing outputs to peripheral devices in medical systems devices, said method comprising:
   providing an instruction to control a peripheral device;
   creating a data object based on the instruction;
   storing the data object in a second memory to be output to the peripheral device, wherein the second memory is not a component of the peripheral device;
   storing the data object in a first memory instead of the second memory if the peripheral device is not accessible and not available to accept the data object, wherein the first memory stores the data object for a longer time period than the second memory; and
   automatically determining whether the peripheral device is available to accept the data object after the data object has been stored in the first memory.

2. A method in accordance with claim 1 further comprising
   determining whether the peripheral device is available to accept the data object before instructing to store the data object in the first memory; and
   transferring the data object from the second memory to the first memory upon determining that the peripheral device is not available.

3. A method in accordance with claim 1 further comprising enabling a user to access the data object from the first memory.

4. A method in accordance with claim 1 further comprising:
   acknowledging that the data object is received by the peripheral device if the data object is received by the peripheral device.

5. A method in accordance with claim 1 wherein said providing the instruction to control the peripheral device comprises one of:
   instructing to print at least one of text, a report and images;
   instructing to record to a video cassette recorder;
   instructing to electronically mail a copy of images to a remote location;
   instructing to create a copy of the images on one of a floppy disk, a magneto-optical disk, a compact disc, a flash memory card, and a digital versatile disc; and
   instructing to create a copy of a patient's information on the digital versatile disc.

6. A method in accordance with claim 1 wherein said creating the data object based on the instructions comprises one of:
   creating a first data object that instructs to print;
   creating a second data object that instructs to record to a video cassette recorder;
   creating a third data object that instructs to electronically mail a copy of images to a remote location;
   creating a fourth data object that instructs to create a copy of images on one of a floppy disk, a magneto-optical disk, and a digital versatile disc; and
   creating a fifth data object that instructs to create a copy of a patient's information on the digital versatile disc.

7. A method in accordance with claim 1 wherein a processor is configured to create the data object based on the instructions and wherein said storing the data object in the first memory if the peripheral device that provides the output is not available to accept the data object comprises:
   storing the data object in the first memory if the peripheral device that provides the output is at least one of deenergized, operationally de-coupled from the processor, and unoperational.

8. A method in accordance with claim 1 wherein said automatically determining whether the peripheral device is available to accept the data object after the data object has been stored in the first memory comprises:
   repeatedly determining whether the peripheral device is available to accept the data object until the peripheral device is available to accept the data object.

9. An imaging system comprising:
   a source configured to transmit medical imaging signals; and
   a processor operationally coupled to said source, said processor configured to:
   receive an instruction to control a peripheral device;
   create a data object based on the instruction;
   instruct to store the data object in a second memory to be output to the peripheral device;
   instruct to store the data object in a first memory instead of the second memory if the peripheral device is not in an active state and not available to accept the data object, wherein the first memory stores the data object for a longer time period than the second memory; and
   automatically determine whether the peripheral device is available to accept the data object after the data object has been stored in the first memory.

10. An imaging system in accordance with claim 9 wherein said processor is configured to:
   determine whether the peripheral device is available to accept the data object before instructing to store the data object in said first memory; and
   transfer the data object from said second memory to said first memory on determining that said peripheral device is not available.

11. An imaging system in accordance with claim 9 wherein said processor is configured to perform one of:
   enable a user to obtain the data object from said first memory; and
   automatically obtain the data object from said first memory.

12. An imaging system in accordance with claim 9 wherein said processor is configured to:
   receive an acknowledgment that the data object is received by said peripheral device if the data object is received by said peripheral device.

13. An imaging system in accordance with claim 9 wherein to receive the instruction to control the peripheral device, said processor configured to perform one of:
   receive an instruction to print;
   receive an instruction to record to a video cassette recorder;
   receive an instruction to electronically mail a copy of images to a remote location;
   receive an instruction to create a copy of images on one of a floppy disk, a magneto-optical disk, and a digital versatile disc; a flash memory card, a compact disc, and
   receive an instruction to create a copy of a patient's information on said digital versatile disc.

14. An imaging system in accordance with claim 9 wherein to create the data object based on the instructions said processor configured to perform one of:
   create a first data object that instructs to print;
   create a second data object that instructs to record to a video cassette recorder;
   create a third data object that instructs to electronically mail a copy of images to a remote location;
   create a fourth data object that instructs to create a copy of images on one of a floppy disk, a magneto-optical disk, and a digital versatile disc; and
   create a fifth data object that instructs to create a copy of a patient's information on said digital versatile disc.

15. An imaging system in accordance with claim 9 wherein to instruct to store the data object in said first memory if said peripheral device that provides the output is not available to accept the data object said processor is configured to:
   instruct to store the data object in said first memory if said peripheral device that provides the output is at least one of de-energized, operationally de-coupled from said processor, and unoperational.

16. An imaging system in accordance with claim 9 wherein to automatically determine whether said peripheral device is available to accept the data object after the data object has been stored in said first memory said processor is configured to:
   repeatedly determine whether said peripheral device is available to accept the data object until said peripheral device is available to accept the data object.

17. The imaging system in accordance with claim 9, wherein said source is a component of at least one of an ultrasound imaging system, an electron-beam tomography (EBT) imaging system, a magnetic resonance imaging (MRI) system, a single photon emission computed tomography (SPECT) imaging system, a computed tomography (CT) imaging system, and a positron emission tomography (PET) imaging system.

18. A non-transitory computer-readable medium encoded with a program configured to:
   receive an instruction to control a peripheral device;
   create a data object based on the instruction;
   instruct to store the data object in a second memory to be output to the peripheral device, wherein the second memory is not a component of the peripheral device;

instruct to store the data object in a first memory instead of the second memory if the peripheral device is not accessible and not available to accept the data object, wherein said first memory stores the data object for a longer time period than the second memory; and automatically determine whether the peripheral device is available to accept the data object after the data object has been stored in the first memory.

19. A non-transitory computer-readable medium in accordance with claim 18 wherein said program is configured to determine whether the peripheral device is available to accept the data object before instructing to store the data object in said first memory; and transfer the data object from said second memory to said first memory on determining that said peripheral device is not available.

20. A non-transitory computer-readable medium in accordance with claim 18 wherein said program is configured to enable a user to obtain the data object from said first memory.

21. A non-transitory computer-readable medium in accordance with claim 18 wherein said program is configured to:

receive an acknowledgment that the data object is received by said peripheral device if the data object is received by said peripheral device.

\* \* \* \* \*